Figure 1:
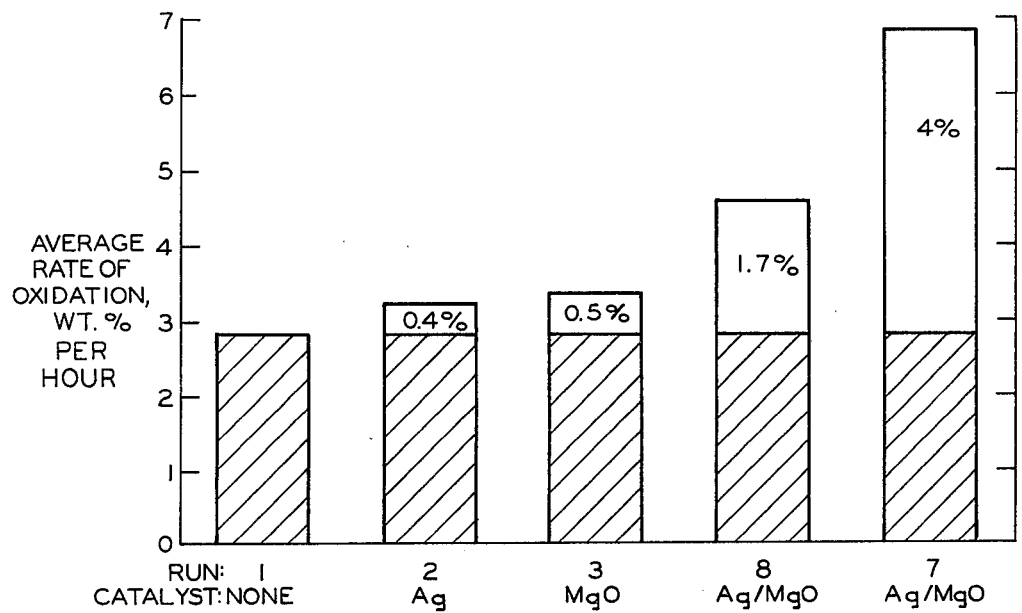

United States Patent [19]

Wu et al.

[11] 4,201,875

[45] May 6, 1980

[54] CATALYST AND PROCESS FOR PRODUCING HYDROPEROXIDES

[75] Inventors: Yulin Wu; Marvin M. Johnson; Gerhard P. Nowack, all of Bartlesville, Okla.

[73] Assignee: Phillips Petroleum Company, Bartlesville, Okla.

[21] Appl. No.: 930,077

[22] Filed: Aug. 1, 1978

[51] Int. Cl.² .......................................... C07C 179/02
[52] U.S. Cl. ..................................................... 568/575
[58] Field of Search ................................ 568/574, 575

[56] References Cited

U.S. PATENT DOCUMENTS

| | | | |
|---|---|---|---|
| 2,632,773 | 3/1953 | Armstrong et al. | 568/574 |
| 2,730,550 | 1/1956 | Fortuin et al. | 568/575 |
| 2,749,368 | 6/1956 | Fortuin | 568/575 |
| 2,820,832 | 1/1958 | Bernis | 568/575 |
| 3,524,888 | 8/1970 | Dressler et al. | 568/575 |

FOREIGN PATENT DOCUMENTS

| | | | |
|---|---|---|---|
| 510517 | 3/1955 | Canada | 568/575 |
| 5443534 | 7/1957 | Canada | 568/575 |

OTHER PUBLICATIONS

Journal of Catalysis vol. 20, pp. 401–411 (1971).

Primary Examiner—Werren B. Lone

[57] ABSTRACT

Organic hydroperoxides are prepared by reacting an organic compound with oxygen in the presence of a novel catalyst comprising metallic silver supported upon an inorganic support selected from the oxides and carbonates of metals of Groups IIa, IIb, IIIb, and IVb.

26 Claims, 1 Drawing Figure

CATALYST AND PROCESS FOR PRODUCING HYDROPEROXIDES

This invention relates to the production of organic hydroperoxides.

It is known that compounds possessing a carbon-hydrogen bond can be oxidized with molecular oxygen to products containing a hydroperoxide group where the original carbon-hydrogen bond was located. Depending upon the particular starting compound, hydroperoxides can be produced with rather high selectivity under suitable oxidation conditions. At the same time, it is recognized that in order to achieve a reasonable degree of selectivity to the desired hydroperoxide, relatively mild conditions need to be utilized because under more severe conditions oxidation of the starting compound can proceed in a nonselective manner and can oxidize the starting compound to such products as carbon dioxide and water under extreme conditions. Under the relatively mild conditions needed for the selective oxidation of the starting compounds to hydroperoxides a penalty is then exacted from the process in terms of the relatively slow reaction rate for the oxidation reaction. Hence, it is desirable to provide a relatively selective oxidation reaction for the production of hydroperoxides while at the same time attaining a faster rate of oxidation under the relatively mild conditions utilized.

Accordingly an object of the present invention is to provide an improved method for producing hydroperoxide compounds.

Another object of the present invention is to provide an increase in the reaction rate in a process for producing hydroperoxides.

Another object of the present invention is to provide an improved process for the production of cyclohexylbenzene hydroperoxides by the oxidation of cyclohexylbenzene.

Still another object of the instant invention is to provide a novel catalyst composition which improves the reaction rate in processes for producing hydroperoxides.

Other objects and advantages of the present invention will be apparent from the following disclosure and the appended claims.

In accordance with the present invention hydroperoxides are produced by reacting an organic compound with oxygen in the presence of a catalyst comprising metallic silver supported on an inorganic support selected from the group consisting of at least one of the oxides and carbonates of metals of Groups IIa, IIb, IIIb, and IVb of the Periodic Table as presented in the Handbook of Chemistry and Physics, published by the Chemical Rubber Company, 45th Edition, 1964, page B-2.

Further, in accordance with the present invention there is provided a novel catalyst composition comprising metallic silver supported on an inorganic support of the type set forth in the preceding paragraph.

The instant invention is believed to be broadly applicable to the oxidation of any organic compounds containing at least one carbon-hydrogen bond capable of being oxidized to a hydroperoxide-carbon bond.

Included among the organic compounds that can be oxidized in accordance with the present invention are polymers having suitable hydrogen-carbon bonds. The preferred polymer starting materials are those consisting essentially of carbon and hydrogen. Especially preferred polymers are polymers of conjugated dienes that have had at least a portion of their unsaturation subjected to hydrogenation. Such hydrogenated polymers of conjugated diolefins and methods for preparing them are known in the art. When polymers are oxidized in accordance with the present invention, the product will be a polymeric hydroperoxide which, of course, may contain more than one hydroperoxide group per polymer molecule. Such polymeric hydroperoxides have utility as polymeric initiator species for free radical type reactions and can serve as the base polymer for graft polymerization reactions utilizing the hydroperoxide group as a reaction site in the polymer chain.

Another class of organic compound which can be used as the starting material in the present invention includes organic compounds having the formula

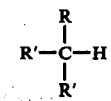

wherein R is hydrogen, an alkyl radical, or an aromatic radical, each R' is individually selected from hydrogen or hydrocarbyl alkyl radical, or the two R' groups are joined to form a saturated hydrocarbyl carbocyclic ring. The preferred compounds have from 3 to 50 carbon atoms. A particularly preferred class of compounds having that formula are the hydrocarbyl compounds having from 3 to 30 carbon atoms. Examples of such hydrocarbyl compounds include propane, 2-methylpropane, 4-methylheptane, 6,8-dipentyleicosane, cyclopentane, cyclohexane, cyclooctane, cyclododecane, methylcyclopentane, 1,4-dimethylcyclohexane, cyclohexylbenzene, and the like.

A particularly preferred class of organic compounds of the formula

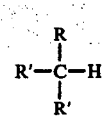

as above defined, are those aromatic compounds having 8 to 50 carbon atoms per molecule where R is an aromatic radical. The aromatic radical can include any sort of substitution that does not prevent the oxidation of the present invention. Examples of suitable substituents include halogen, nitro, alkyl, carboxyalkyl and the like. Examples of such compounds include toluene, p-xylene, m-xylene, ethylbenzene, p-chlorotoluene, p-nitrotoluene, 3-(4-methylphenyl)propanoic acid, isopropylbenzene, cyclopentylbenzene, cyclohexylbenzene, and the like. The most preferred of these aromatic compounds are the hydrocarbyl aromatic, i.e., those containing only carbon and hydrogen.

The molecular hydroperoxides like the polymeric hydroperoxides generally have utility as initiators in free radical polymerization systems. Furthermore, generally such hydroperoxides can be treated further under acidic hyrolysis conditions to provide cleavage products such as hydroxy compounds or carbonyl compounds. In addition such hydroperoxides generally can also be utilized as catalyst components for the epoxidation of olefinic compounds in the presence of tungsten or molybdenum or their compounds.

The catalyst which is utilized in the present invention to provide an increase in the rate of oxidation in the production of hydroperoxide compounds comprises metallic silver supported on an inorganic support selected from the group consisting of at least one of the oxides and carbonates of metals of Groups IIa, IIb, IIIb, and IVb. This invention is based upon the discovery that when metallic silver is supported upon such inorganic supports a synergistic effect upon the oxidation rate is provided which results in an oxidation rate which is generally quite superior to that obtained with catalysts comprising metallic silver supported upon inorganic supports of a more acidic nature such as silicon dioxide, alumina, and the like. Examples of suitable inorganic supports for use in accordance with this invention include calcium oxide, magnesium oxide, barium oxide, zirconium oxide, zinc oxide, lanthanum oxide, thorium oxide, calcium carbonate, magnesium carbonate, and the like, and mixtures thereof. These supports can be utilized in the form of powders, pellets, granules, pills, extrudates, and the like, and as mixtures thereof.

Although the novel effect of this invention is most notable for catalysts consisting essentially of metallic silver and the described inorganic support, it is also within the scope of this invention to employ catalysts in which silver is combined with other metals which are capable as serving as oxidation catalysts for hydroperoxide production. An example, includes catalysts consisting essentially of a silver-gold alloy supported on the described inorganic support.

The supported catalysts of this invention can be prepared by any of the methods well known in the art. For example, the supported catalysts can be prepared by dry mixing the components or by impregnating the support with a solution or dispersion of silver or silver alloy in elemental form or in the form of reducible compounds thereof. Examples of suitable hydrogen reducible compounds include the acetates, nitrates, benzoates, and the like, and mixtures thereof. The impregnated support can be reduced in the presence of hydrogen. Reducible compounds of silver and other metal such as gold can be codeposited on the support or can be deposited separately in any order and then reduced in the presence of hydrogen for the preparation of silver-gold alloy catalysts.

Examples of suitable supported catalysts for the practice of this invention include silver on calcium oxide, silver on magnesium oxide, silver on barium oxide, silver on zirconium oxide, silver on thorium oxide, silver on zinc oxide, silver on magnesium carbonate, silver on zinc oxide and calcium carbonate, silver on lanthanum oxide, 5/95 weight ratio of Au/Ag on magnesium oxide, and the like.

The amount of silver metal present in the supported catalyst can range widely but generally will be in the range of from about 0.05 to about 10 weight % silver and preferably from about 0.5 to about 5 weight % silver with all percentages being based on the total weight of support and silver.

In the oxidation reaction of this invention, the amount of supported catalyst utilized in any catalytically effective amount. Generally this amount is in the range of from about 0.001 to about 10% and preferably from about 0.01 to about 5% by weight based on the starting reactant material.

Any suitable amount of oxygen can be employed. Preferably, enough oxygen is employed to obtain maximum conversion of the organic reactant or reactants. The amount of oxygen employed can be expressed in terms of the mole ratio of oxygen to that of organic compound that is to be oxidzied. Generally, this ratio is in the range of from about 0.005/1 to about 20/1 or higher, and preferably in the range of about 0.01/1 to about 2/1. The oxygen may be introduced into the reaction zone in any manner that will result in oxygen contacting the material to be oxidized. For example, the reaction mixture can be merely stirred under an oxygen atmosphere or oxygen can be bubbled through the reaction mixture. Air as well as other mixtures of gases with oxygen may be utilized as the source of oxygen.

The pressure utilized can be atmospheric or superatmospheric and will generally range from about 0 to about 1000 psig and will preferably range from about 50 to about 400 psig.

The temperature utilized in the instant invention can vary widely. Of course as mentioned earlier, lower temperatures tend to result in better selectivity to hydroperoxides. Generally, the temperature should be in the range of about 25° C. to about 200° C., preferably about 90° C. to about 160° C. The time employed depends only upon the temperature employed and the degree of conversion that one desires. At prolonged times, the yield of hydroperoxides increases reaching a maximum and then declines because of decomposition of the hydroperoxides. Generally, the reaction is conducted for a time in the range of about 5 minutes to about 2 days.

If desired, a reaction diluent may be employed when carrying out the oxidation reaction according to the instant invention. Compounds such as the lower alcohols, e.g. the monohydric alcohols having from 1 to 8 carbon atoms, linear alkane hydrocarbons of from 4 to 12 carbon atoms, and sulfolane can be utilized as diluents for the reaction.

The charge order utilized in the reaction of the instant invention is not particularly critical. However, it is often desirable to utilize a portion of the previous reaction mixture as an ingredient in the charge of a fresh batch of reactant since this often eliminates an induction period that might occur otherwise. In this regard, induction periods can also be essentially elminated by addition of a small amount of a hydroperoxide other than the hydroperoxide product expected if so desired. In this context the added hydroperoxide is called an initiator. Hydroperoxides that are suitable initiators are those which decompose under the reaction conditions quickly enough to reduce the induction periods. Examples of suitable initiators include cumene hydroperoxide and cyclohexylbenzene hydroperoxide. Generally, hydroperoxide initiators are effective in amounts in the range of about 0.5 to about 1.5 weight percent of the weight of the material to be oxidized.

The oxidation reaction of this invention can be carried out in any batch or continuous reactor that is capable of withstanding the pressures and oxidizing conditions which are present. The reaction vessel can be lined with materials such as glass or ceramics or constructed of materials such as stainless steel, Monel, titanium, Inconel and the like. In a continuous process, the reagents can be conveniently passed through the reaction zone containing the supported catalysts and the reactor effluent then treated to remove the hydroperoxide product or sent to a further processing stage.

The reaction mixtures obtained according to the instant invention contain the desired hydroperoxide compound besides unreacted starting material and small amounts of other byproducts along with the catalyst and reaction diluent if such was utilized. One convenient procedure for recovering the hydroperoxide compound from said reaction mixture utilizes a filtration step to remove the catalyst and treatment of the reaction mixture with a mixture of methanol and water which effectively extracts the hydroperoxide compound from the reaction mixture. Subsequently, the aqueous methanol extract can be evaporated to provide the hydroperoxide compound.

Alternately, the reaction mixture can be filtered and used directly in an acid cleavage step if the production of other materials is desired.

The present invention and its advantages will be further understood by reference to the following examples. In these examples, unless it is noted otherwise, weight percent values are based upon the weight of the cyclohexylbenzene reactant.

The supported inventive catalysts in the following examples were prepared by depositing the silver as the nitrate from an aqueous solution onto the support. The impregnated support was then reduced in the presence of hydrogen to provide the supported metallic silver catalysts.

EXAMPLE I

A series of 6 control runs was carried out in which cyclohexylbenzene (CHB) was oxidized at 120° C. in a stirred (2000 rpm) 300 ml stainless steel autoclave under an initial oxygen pressure of 200 psig (1379 kPa). In each run, the autoclave was charged with 60 grams of cyclohexylbenzene, 1 to 1.5 weight % (based on the CHB weight) of an oxidation initiator (cyclohexylbenzene hydroperoxide), and a silver catalyst (as a powder, about 100 mesh) or a support material (as a powder), if used. The results of these control runs are presented below in Table I.

TABLE I

| Run No. | Catalyst Metal/Support | g. | Reaction Time, Hr. | Aug. Rate of Oxidation[a] Wt. %/Hr. | CHB Conv Mole % | Selectivity to Hydroper-Oxide[b] Mole % |
|---|---|---|---|---|---|---|
| 1 | none/none | — | 4.25 | 2.8 | 11.4 | 90 |
| 2 | Ag/none | 0.03 | 4.5 | 3.2 | 12.9 | 98 |
| 3 | none/MgO | 4.8 | 6.0 | 3.3 | 21.5 | 81 |
| 4 | none/MgO | 5.0 | 6.0 | 3.2 | 18.0 | 94 |
| 5 | none/ZrO2 | 1.5 | 5.0 | 1.2 | 7.1 | 71 |
| 6 | none/MgCO3 | 0.06 | 5.85 | 2.8 | 14.9 | 90 |

[a] Average rate of cyclohexylbenzene hydroperoxide production in weight %/hour based on the total reaction mixture. The value is based on an iodometric titration of weighed samples of the reaction mixture.
[b] Mole % selectivity to cyclohexylbenzene hydroperoxide based on the amount of CHB converted.

The results obtained for run 1 show a relatively low rate of oxidation occurs in the absence of a catalyst. The results of run 2 show an increase in the average rate of oxidation (compared with the oxidation rate in run 1) in the presence of silver powder catalyst. Oxidation runs in the presence of magnesium oxide (runs 3 and 4) resulted in a higher rate of oxidation than in control run 1. Zirconium oxide (run 5) was found to be detrimental to the oxidation rate and magnesium carbonate (run 6) had no significant effect on the oxidation rate.

EXAMPLE II

Several runs were carried out according to the instant invention utilizing silver on magnesium oxide or magnesium carbonate supports as the oxidation catalyst. In each run, the oxidation of cyclohexylbenzene was carried out in a 300 ml stainless steel autoclave under an initial oxygen pressure of 200 psig (1379 kPa). Each of the runs utilized 60 g. of cyclohexylbenzene and 1 to 1.7 weight % of the oxidation initiator (cyclohexylbenzene hydroperoxide). The results obtained in the oxidation runs of this example are presented below in Table II.

TABLE II

| Run No. | Catalyst[a] Metal/Support | g. | Reaction Temp., °C. | Reaction Time, hr. | Avg. Rate of Oxidation,[b] Wt. %/hr. | CHB Conv. mole % | Selectivity to Hydroperoxide,[c] mole % |
|---|---|---|---|---|---|---|---|
| 7 | Ag/MgO | 0.1 | 120° | 2.12 | 6.8 | 14.4 | 88 |
| 8 | Ag/MgO | 0.5 | 120° | 3.38 | 4.5 | 14.3 | 93 |
| 9 | Ag/MgO | 1.2 | 120° | 2.25 | 6.4 | 14.2 | 92 |
| 10 | Ag/MgO | 1.2 | 100° | 7.25 | 1.0 | 6.7 | 99 |
| 11 | Ag/MgO | 1.2 | 110° | 6.0 | 2.5 | 14.2 | 94 |
| 12 | Ag/MgCO3 | 1.0 | 120° | 0.85 | 12.3 | 13.3 | 70 |

[a] 5 weight % silver on the support.
[b] See footnote (a) of Table I.
[c] See footnote (b) of Table I.

The results shown in Table II demonstrate that the oxidation of cyclohexylbenzene to cyclohexylbenzene hydroperoxide in the presence of silver on magnesium oxide (runs 7, 8, 9) or on magnesium carbonate (run 12) supports proceeds at a significantly higher rate of oxidation than the control run (run 1) in the absence of a catalyst. Oxidation of cyclohexylbenzene also occurs at lower reaction temperatures (runs 10 and 11) in the presence of silver on magnesium oxide.

The significant advantage of the supported silver catalysts of this invention is most clearly shown by refering to the bar graph of accompanying FIG. 1. FIG. 1 presents a bar graph illustrating the relative difference in oxidation rates obtained with no catalyst, with the separate components of the inventive catalyst, and with the inventive catalyst.

Run 1 was conducted in the absence of a catalyst or support and had an average rate of oxidation of 2.8 weight % per hour. This can be considered the thermally induced rate of reaction at 120° C. Runs in the presence of silver (run 2) or magnesium oxide (run 3) have slightly higher oxidation rates than run 1. The portion of the reaction rate attributed to a thermal reaction is taken from run 1 and is indicated in each bar in FIG. 1 as a shaded area. The unshaded area of the bar is the portion of the oxidation rate that results from the presence of the added catalyst or support material. Therefore, the presence of silver in the oxidation reaction increased the oxidation rate by 0.4 weight % per hour and the presence of magnesium oxide increased the rate of oxidation by 0.5 weight % per hour over the rate expected for thermal oxidation. The presence of the silver catalyst on the magnesium oxide support resulted in an increase in oxidation rate of 1.7 weight % per hour in run 8 and about 4 weight % per hour in run 7 over the rate expected for thermal oxidation and this increase in oxidation rate is significantly higher than an increase predicted by the total of increases in oxidation rate obtained for silver alone and magnesium oxide alone (0.4+0.5=0.9 weight % per hour).

In a similar manner, the silver on magnesium carbonate catalyst (run 12) gave a much larger increase in oxidation rate (12.3 weight % per hour−2.8 weight % per hour for thermal reaction of run 1=9.5 weight % per hour increase) than would be expected from the combined increases in oxidation rate obtained for silver alone and magnesium carbonate alone (0.4+0.0=0.4 weight % per hour).

EXAMPLE III

Additional runs were carried out according to the instant invention utilizing silver on various supports. In the runs of this example, the oxidation reactions were carried out utilizing a 300 ml stainless steel autoclave reactor at 120° C. under an initial oxygen pressure of 200 psig (1379 kPa). In each run, the starting material to be oxidized was cyclohexylbenzene (60 g.) and about 1 weight % of the oxidation initiator (cyclohexylbenzene hydroperoxide) was present. The results of these runs were shown below in Table III.

TABLE III

| Run No. | Catalyst[a] Metal/Support | g. | Reaction Time, Hr. | Avg. Rate % Oxidation, Wt. %/hr. | CHB Conv. Mole % | Selectivity to Hydroperoxide, Mole % |
|---|---|---|---|---|---|---|
| 13 | Ag/ZrO$_2$ | 0.1 | 5.5 | 3.7 | 15.6 | 96 |
| 14 | Ag/ZrO$_2$ | 0.6 | 4.1 | 3.8 | 14.3 | 95 |
| 15 | Ag/ZrO$_2$ | 1.2 | 3.4 | 4.6 | 15.4 | 90 |
| 16 | Ag/ZnO | 0.6 | 2.4 | 5.9 | 13.9 | 89 |
| 17 | Ag/ZnO-CaCO$_3$[b] | 0.6 | 0.68 | 15.3 | 14.8 | 62 |
| 18 | Ag/CaAl$_2$O$_4$ | 0.6 | 4.3 | 3.9 | 17.8 | 82 |

[a] 5 weight % silver on the support.
[b] The support contains about 80 weight % ZnO and about 20 weight % CaCO$_3$ based on the total weight of the support.

The results of these runs show that the rate of oxidation of cyclohexylbenzene in the presence of a silver catalyst on zirconium oxide or zinc oxide supports (runs 13–16) is increased over control runs which utilized either no catalyst (run 1) or an unsupported silver catalyst (run 2). This is considered surprising because zirconium oxide by itself is detrimental to the oxidation reaction and results in a decrease in oxidation rate (run 5) compared with the uncatalyzed reaction in run 1.

Run 17 shows that a silver catalyst on a mixed support (zinc oxide and calcium carbonate) results in a large increase in oxidation rate over control runs 1 and 2, but a reduced selectivity to the hydroperoxide product was also observed.

Run 18 utilized silver on calcium aluminate, a support that contains both basic (Ca) and acidic (Al) components. Although the rate of oxidation in this run is above the rate for a thermal reaction (run 1) or the rate for a reaction with silver only, the selectivity to hydroperoxide is low and indicates that the presence of an acidic material within the support is less desirable than the presence of only basic materials.

EXAMPLE IV

A control run was carried out utilizing a silver catalyst on a support outside the scope of this invention. This oxidation run was carried out in a 300 ml stainless steel autoclave at 120° C. under an initial oxygen pressure of 200 psig (1379 kPa). The oxidation substrate was cyclohexylbenzene (60 g.) and 1 weight % of the oxidation initiator (cyclohexylbenzene hydroperoxide) was present.

Run 19 utilized 0.5 g. of a catalyst containing 5 weight % silver on silicon dioxide. At the conclusion of the 5 hour reaction time, the average rate of oxidation was determined to be 1.31 weight % per hour. The conversion of CHB was 6.7 mole % and the selectivity to cyclohexylbenzene hydroperoxide was 84 mole %. These results indicate that the use of silicon dioxide, an acidic material that is outside the scope of this invention, as a support for the silver catalyst results in an oxidation rate significantly below the rate of the uncatalyzed oxidation of CHB (run 1).

From the foregoing description one skilled in the art can easily ascertain the essential characteristics of this invention and without departing from the spirit and scope thereof adapt this invention to various usages and conditions other than those specifically set forth in the above examples. Accordingly, it is noted that the foregoing examples should not be viewed as limiting the claimed invention.

We claim:
1. A process for producing an organic hydroperoxide comprising reacting an organic compound having at least one carbon-hydrogen bond capable of being oxidized to a hydroperoxide-carbon bond with oxygen in the presence of a catalyst comprising metallic silver or silver-gold alloy supported on an inorganic support selected from the group consisting of at least one of the oxides and carbonates of metals of Groups IIa, IIb, IIIb, and IVb wherein said organic compound is selected from the group consisting of (1) hydrogenated polymers of conjugated diolefins and (2) organic compounds having 3 to 50 carbon atoms and the general formula

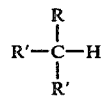

wherein R is hydrogen, an alkyl radical, or an aromatic radical, each R' is individually selected from hydrogen or an alkyl radical, or the two R' groups are joined to form a saturated hydrocarbyl ring, and wherein said reaction is carried out at a temperature in the range of about 25° C. to about 200° C.

2. A process according to claim 1 wherein said inorganic support is selected from the group consisting of calcium oxide, magnesium oxide, barium oxide, zirconium oxide, zinc oxide, lanthanum oxide, thorium oxide, calcium carbonate, magnesium carbonate, and mixtures thereof.

3. A process according to claim 2 wherein said inorganic support is selected from the group consisting of magnesium oxide, magnesium carbonate, zirconium oxide, zinc oxide, and a zinc oxide-calcium carbonate mixture.

4. A process according to claim 3 wherein said catalyst consists essentially of metallic silver supported on said inorganic support.

5. A process according to claim 4 wherein the amount of silver in said catalyst is in the range of from about 0.05 to about 10 weight percent based upon the total weight of the catalyst, the amount of catalyst employed is in the range of about 0.001 to about 10 weight percent of the weight of said organic compound, the mole ratio of oxygen to said organic compound is in the range of from about 0.005/1 to about 20/1, and the pressure is in the range of about 0 to about 1000 psig.

6. A process according to claim 5 wherein said organic compound is selected from the group consisting of hydrocarbons having 3 to 30 carbon atoms and the general formula

wherein R is hydrogen, an alkyl radical, or an aromatic radical, each R' is individually selected from hydrogen or an alkyl radical, or the two R' groups are joined to form a saturated hydrocarbon carbocyclic ring.

7. A process according to claim 6 wherein said organic compound is selected from the group consisting of propane, 2-methylpropane, 4-methylheptane, 6,8-dipentyleicosane, cyclopentane, cyclohexane, cyclooctane, cyclododecane, methylcyclopentane, 1,4-dimethylcyclohexane, toluene, p-xylene, m-xylene, ethylbenzene, isopropylbenzene, cyclopentylbenzene, and cyclohexylbenzene.

8. A process according to claim 7 wherein said organic compound is cyclohexylbenzene.

9. A process according to claim 8 wherein said support is magnesium oxide.

10. A process according to claim 8 wherein said support is magnesium carbonate.

11. A process according to claim 8 wherein said support is zirconium oxide.

12. A process according to claim 8 wherein said support is a zinc oxide-calcium carbonate mixture.

13. A process according to claim 8 wherein said support is zinc oxide.

14. A process according to claim 3 wherein said catalyst consists essentially of a silver-gold alloy supported on said inorganic support.

15. A process for the production of cyclohexylbenzene hydroperoxide comprising contacting cyclohexylbenzene in the liquid phase with a gas containing free oxygen in the presence of a catalyzing amount of a catalyst comprising metallic silver or silver-gold alloy supported on an inorganic support selected from the group consisting of at least one of the oxides and carbonates of metals of Groups IIa, IIb, IIIb, and IVb, wherein said contacting is carried out under reaction conditions such that cyclohexylbenzene hydroperoxide is produced, said reaction conditions including a temperature in the range of about 25° C. to about 200° C. and a pressure of about 0 to about 1000 psig.

16. A process according to claim 15 wherein the amount of silver in said catalyst is in the range of about 0.05 to about 10 weight percent based upon the total weight of the catalyst and the amount of catalyst employed is in the range of about 0.001 to about 10 weight percent of the weight of said cyclohexylbenzene.

17. A process according to claim 16 wherein the temperature is in the range of about 90° C. to about 160° C.

18. A process according to claim 17 wherein said inorganic support is selected from the group consisting of magnesium oxide, magnesium carbonate, zirconium oxide, zinc oxide, and a zinc oxide-calcium carbonate mixture.

19. A process according to claim 18 wherein said catalyst consists essentially of metallic silver supported on said inorganic support.

20. A process according to claim 19 wherein said support is magnesium oxide.

21. A process according to claim 19 wherein said support is magnesium carbonate.

22. A process according to claim 19 wherein said support is zirconium oxide.

23. A process according to claim 19 wherein said support is zinc oxide.

24. A process according to claim 19 wherein said support is a mixture of zinc oxide and calcium carbonate.

25. A process according to claim 24 wherein the weight ratio of calcium carbonate to zinc oxide is about 1 to 4.

26. A process according to claim 18 wherein said catalyst consists essentially of a silver-gold alloy supported in said inorganic support.

* * * * *